(12) United States Patent
Jacobsen et al.

(10) Patent No.: US 8,516,918 B2
(45) Date of Patent: Aug. 27, 2013

(54) BIOMIMETIC MECHANICAL JOINT (75) Inventors: Stephen C. Jacobsen, Salt Lake City, UT (US); Marc X. Olivier, Sandy, UT (US); Brian J. Maclean, Salt Lake City, UT (US)

(73) Assignee: Raytheon Company, Waltham, MA (US)

( * ) Notice: Subject to any disclaimer, the term of this patent is extended or adjusted under 35 U.S.C. 154(b) by 255 days.

(21) Appl. No.: 13/061,482

(22) PCT Filed: Aug. 28, 2009

(86) PCT No.: PCT/US2009/055429
§ 371 (c)(1),
(2), (4) Date: May 24, 2011

(87) PCT Pub. No.: WO2010/025409
PCT Pub. Date: Mar. 4, 2010

(65) Prior Publication Data
US 2011/0214524 A1 Sep. 8, 2011

Related U.S. Application Data (60) Provisional application No. 61/092,699, filed on Aug. 28, 2008.

(51) Int. Cl.
*B25J 17/00* (2006.01)
(52) U.S. Cl.
USPC ......... 74/490.01; 74/490.05; 901/14; 901/21; 901/28; 901/1

(58) Field of Classification Search
USPC ............... 74/490.01, 490.02, 490.03, 490.04, 74/490.05; 901/1, 14, 21, 23, 27, 28, 50
See application file for complete search history.

(56) References Cited

U.S. PATENT DOCUMENTS

| 4,955,918 A | 9/1990 | Lee |
| 5,092,646 A * | 3/1992 | Smallridge .................. 294/111 |

(Continued)

FOREIGN PATENT DOCUMENTS

| EP | 1535705 | 6/2005 |
| JP | 2001287177 | 10/2001 |
| WO | WO 98/30177 | 7/1998 |

OTHER PUBLICATIONS

U.S. Appl. No. 13/061,472, filed May 23, 2011; Stephen C. Jacobsen.

(Continued)

*Primary Examiner* — David M Fenstermacher
(74) *Attorney, Agent, or Firm* — Thorpe North & Western LLP (57) ABSTRACT

A biomimetic mechanical joint for generating a variable torque between support members of a biomimetic robotic device, including a base support member, a rotary support member rotatably coupled to the base support member, and a variable-radius pulley operably coupled between the base support member and rotary support member. The variable-radius pulley comprises a sheave body having a variable radius and one or more tendon grooves formed in the circumferential outer surface. The mechanical joint further includes one or more flexible tendons and antagonistic actuator pairs, with each actuator pair being coupled to one or more tendons and configured to operate the tendon around the variable-radius pulley in either direction to create a variable torque between the base and rotary support members.

20 Claims, 3 Drawing Sheets

(56) References Cited

U.S. PATENT DOCUMENTS

| | | | |
|---|---|---|---|
| 5,207,114 A * | 5/1993 | Salisbury et al. | 74/479.01 |
| 5,282,460 A | 2/1994 | Boldt | |
| 5,502,363 A | 3/1996 | Tasch et al. | |
| 5,549,712 A | 8/1996 | Gammer et al. | |
| 5,873,734 A * | 2/1999 | Griswold et al. | 434/274 |
| 5,888,235 A * | 3/1999 | Jacobsen et al. | 623/58 |
| 6,966,882 B2 * | 11/2005 | Horst | 601/5 |
| 7,066,896 B1 | 6/2006 | Kiselik | |
| 7,087,031 B2 * | 8/2006 | Rossi et al. | 602/16 |
| 7,308,848 B2 | 12/2007 | Jacobsen et al. | |
| 7,628,766 B1 * | 12/2009 | Kazerooni et al. | 602/16 |
| 7,935,153 B2 * | 5/2011 | Auberger | 623/43 |
| 8,052,185 B2 * | 11/2011 | Madhani | 294/106 |
| 8,231,687 B2 * | 7/2012 | Bedard et al. | 623/24 |
| 2003/0030397 A1 | 2/2003 | Simmons | |
| 2004/0128028 A1 | 7/2004 | Miyamoto et al. | |
| 2004/0158175 A1 * | 8/2004 | Ikeuchi et al. | 601/5 |
| 2004/0172165 A1 | 9/2004 | Iribe et al. | |
| 2004/0176875 A1 | 9/2004 | Iribe et al. | |
| 2007/0162152 A1 | 7/2007 | Herr et al. | |
| 2007/0162404 A1 | 7/2007 | Gorelik et al. | |
| 2009/0210093 A1 | 8/2009 | Jacobsen | |

OTHER PUBLICATIONS

U.S. Appl. No. 13/061,488, filed Feb. 28, 2011; Stephen C. Jacobsen.
PCT Application PCT/US2009/055440; filed Aug. 28, 2009; Stephen C. Jacobsen; International Search Report mailed Jan. 14, 2011.
PCT Application PCT/US2009/055423; filed Aug. 28, 2009; Stephen C. Jacobsen; International Search Report mailed Dec. 22, 2009.
PCT Application PCT/US2009/055429; filed Aug. 28, 2009; Stephen C. Jacobsen; International Search Report mailed Jan. 8, 2010.

* cited by examiner

BIOMIMETIC MECHANICAL JOINT

RELATED APPLICATIONS

This application claims priority to U.S. Provisional Patent Application No. 61/092,699, filed Aug. 28, 2008, and entitled "Biomimetic Mechanical Joint," which application is incorporated by reference in its entirety herein.

This invention was made with government support under W911NF-05-0111 awarded by the U.S. Army. The government has certain rights in the invention.

FIELD OF THE INVENTION

The field of the invention relates generally to exoskeletons and robots, and more specifically to the mechanical joints for exoskeletons and robots having natural or human-like characteristics.

BACKGROUND OF THE INVENTION AND RELATED ART

Significant advancements in the development of robots and robotic devices have been achieved in recent decades. Manufacturing efficiencies gained through the use of robotic assemblers and manipulators, exploratory robotic vehicles (such as those traveling the surface of Mars), and animatronics characters often seen at theme parks and other sights of attraction are but a few popular examples. Each of these specialized robots have common characteristics, however, in that they do not have true human-like capabilities, nor do they function with human-like operation. Indeed, many robotic devices are tethered to external power sources, while others are configured to move without bi-pedal or human-like locomotion. True mobile and un-tethered humanoid robots and exoskeletons, while in existence, are in the early stages of development, and are continually being improved to better participate in mobile, human-like activities.

One reason for the continuing technological difficulty in advancement of human-like, or biomimetic, robotic systems toward un-tethered humanoid robotic activity is the inefficiency inherent within the mechanical joints that provide the robots with the ability to move. In a robotic device, movement about a mechanical joint is a primary consumer of power. Yet with few exceptions the mechanical joints in robots and human assistance devices have been optimized for control and performance, these taking precedence over optimal efficiency considerations. For instance, many modern non-biomimetic industrial robots perform significant work with the advantage of being permanently connected to external electrical, fluid or mechanical power systems that can supply a surplus of power, leading to articulating joints capable of precise and powerful movements, but which are also highly wasteful of energy.

Efficiency has also suffered in powered prosthetic limbs as these devices have been primarily confined to the laboratory, research centers, or individuals living in populated areas with ready access to sources of power. In a remote work or battlefield environment, however, efficiency is critical for long-term operation and/or survivability, as an exoskeleton or human-like robot is useless if it prematurely runs out of fuel or discharges its batteries. Advancements in more efficient operation of human-like robotic devices or exoskeletons, particularly more efficient operation of the biomimetic joints through a range of movements and load conditions, without sacrificing speed or power, are greatly needed and will serve to provide improved, un-tethered human-like robotic activity.

SUMMARY OF THE INVENTION

The human body can be one model for optimizing the mechanical joints in exoskeletons and human-like robots for efficiency. The bodies of all species in the animal kingdom, including humans, have been evolved over time for highly-efficient operation, in order to function and survive with only a last meal or stored fat for energy. The ability to emulate the efficient movement of a human limb around a natural joint can be provided, at least in part, with a biomimetic mechanical joint.

In the present invention, this includes the ability to provide a biomimetic mechanical joint that emulates the variable torque provided by a natural joint, which variable torque is needed to efficiently rotate the joint through a range of positions and under a variety of load conditions. With an exoskeleton and human-like robots, the biomimetic mechanical joint can include a variable radius pulley coupled to one or more pairs of antagonistic actuators with one or more flexible tendons, to provide a variable torque when rotating a rotary support member or limb segment that emulates the variable torque provided by a corresponding natural joint.

In accordance with a representative embodiment as broadly described herein, the present invention resides in a biomimetic mechanical joint for emulating the variable torque provided by a natural joint, the mechanical joint comprising a base support member of a robotic device, a rotary support member of the robotic device, and a variable-radius ("VR") pulley rotably coupling the rotary member to the base member. The VR pulley further comprises a sheave body with a circumferential outer surface and a pivot point, the radial distance between the outer surface and the pivot point being variable along a length of the outer surface, one or more tendon grooves formed in the outer surface, and a tendon attachment point formed within the tendon grooves. The mechanical joint also includes one or more flexible tendons, each tendon coupled to the tendon attachment point and having first and second free end portions wrapping around the pulley in opposite directions within the tendon groove. The mechanical joint further includes one or more antagonistic actuator pairs, each actuator pair coupled with a pair of end connectors to the two end portions of a tendon, and where the actuator pair is configured to pull the tendon around the variable-radius pulley in either direction to create a variable torque between the base and rotary support members.

In accordance with another representative embodiment as broadly described herein, the present invention resides in a biomimetic mechanical joint for emulating the variable torque provided by a natural joint, the mechanical joint comprising a base support member of a robotic device, a rotary support member of the robotic device, and a variable-radius ("VR") pulley rotably coupling the rotary member to the base member. The VR pulley further comprises a sheave body with a circumferential outer surface and a pivot point, the radial distance between the outer surface and the pivot point being variable along a length of the outer surface, a tendon groove formed in the outer surface, and one or more tendon attachment points formed within the tendon groove. The mechanical joint also includes one or more flexible tendons coupled to a tendon attachment point and having a free end portion wrapping around the pulley within the tendon groove, and one or more actuators coupled to the free end portion of the tendon and configured to pull the tendon around the variable-radius pulley to create a variable torque between the base and rotary support members.

The present invention also resides in a method of making a biomimetic mechanical joint for generating a variable torque between support members of a robotic device. The method includes obtaining a base support member and a rotary support member, and coupling a variable-radius pulley having a pivot means between the base support member and the rotary support member to facilitate rotation of the rotary support member about the base support member. The method further includes mounting one or more antagonistic actuator pairs to the rotary support member, and installing one or more flexible tendons between the variable-radius pulley and the antagonistic actuator pairs, wherein the actuator pairs activate to pull the tendon around the variable-radius pulley in either direction to create a variable torque between the base and rotary support members.

BRIEF DESCRIPTION OF THE DRAWINGS

Features and advantages of the invention will be apparent from the detailed description that follows, and which taken in conjunction with the accompanying drawings, together illustrate features of the invention. It is understood that these drawings merely depict exemplary embodiments of the present invention and are not, therefore, to be considered limiting of its scope. And furthermore, it will be readily appreciated that the components of the present invention, as generally described and illustrated in the figures herein, could be arranged and designed in a wide variety of different configurations. Nonetheless, the invention will be described and explained with additional specificity and detail through the use of the accompanying drawings, in which.

DETAILED DESCRIPTION OF EXEMPLARY EMBODIMENTS

The following detailed description of the invention makes reference to the accompanying drawings, which form a part thereof and in which are shown, by way of illustration, exemplary embodiments in which the invention may be practiced. While these exemplary embodiments are described in sufficient detail to enable those skilled in the art to practice the invention, it should be understood that other embodiments may be realized and that various changes to the invention may be made without departing from the spirit and scope of the present invention. As such, the following more detailed description of the exemplary embodiments of the present invention is not intended to limit the scope of the invention as it is claimed, but is presented for purposes of illustration only: to describe the features and characteristics of the present invention, and to sufficiently enable one skilled in the art to practice the invention. Accordingly, the scope of the present invention is to be defined solely by the appended claims.

Illustrated in FIGS. 1-7 are various exemplary embodiments of a biomimetic mechanical joint that can be integrated into powered prosthetic limbs, human-like robots, exoskeletons or other biomimetic robotic devices, etc. The biomimetic mechanical joint of the present invention can use a variable-radius ("VR") pulley, in combination with one or more antagonistic actuators, to meet the motion requirements of the mechanical joint about a single degree-of-freedom ("DOF") axis. The present invention can be distinguished from the prior art, which systems typically use a rotary DC motor actuator to generate movement about the same axis. The mechanical advantage provided by a VR pulley allows for the antagonistic actuators to be reduced in size in comparison to similar actuators while providing the same torque. This reduction in size can lead to significant improvements in both efficiency and performance.

As stated above, the present invention can use one or more antagonistic actuators or pairs of antagonistic actuators to power the rotary support member around the base support member. Each antagonistic actuator can comprise two uni-directional actuators arranged antagonistically (e.g. an antagonistic actuator pair) to pull on either end of a tendon that can be coupled at both ends to the antagonistic actuators and at a midsection to a tendon attachment block mounted to the VR pulley. Pulling on either end of the tendon can rotate the VR pulley with respect to the antagonistic actuator, or vice versa. The antagonistic actuator can further comprise a single-acting hydraulic actuator, pneumatic actuator, linear motor, or rotary electric motor, or any other uni-directional actuator (e.g. able to generate a force only one direction).

Alternatively, the single tendon can be sub-divided into two tendons, with one end of each tendon coupled to a tendon attachment point on the VR pulley and the other end of each tendon coupled to one of the actuators in the antagonistic actuator pair. In yet another embodiment of the present invention, the biomimetic mechanical joint can be provided with one or more uni-directional actuators coupled to one or more flexible tendons that connect to tendon attachment points on the same side of the VR pulley, so as to actuate the joint in one direction only and allow an applied load (e.g. a weight under the influence of gravity, etc.) to operate the joint in the opposite direction.

The biomimetic mechanical joint of the present invention can provide significant advantages over prior-related mechanical joints, some of which are recited here and throughout the following more detailed description. First, the biomimetic mechanical joint can be significantly more efficient than the mechanical joints in existing prosthetic limbs, exoskeletons, human-like robots or robotic devices that use a DC motor, etc. to provide a constant torque across the entire range of positions of the joint. A mechanical joint which mimics the natural movement of the human body may have a torque requirement that varies, depending on the position of the support segments relative to gravity and to each other. For instance, less torque can be required to rotate the joints in an artificial leg when walking along a level surface than when standing up from a squatting position. Consequently, constant torque systems sized to the maximum torque operating condition have a disadvantage in that they are oversized for the reduced torque operating condition, and are thus wasteful of energy. By using a variable-radius pulley to create a mechanical advantage between the pulley and the actuation system during the high-torque operating conditions, the actuator can be more-appropriately sized to meet a number of different lower torque operating conditions. In other words, efficiency can be optimized for a specific operating condition.

Efficiency and performance can be further improved if a plurality of fractional antagonistic actuators are used with the VR pulley. A 'fractional' actuator can be defined as an actuator that meets less-than-100% of the maximum potential torque demanded of the mechanical joint, which is the standard design point for most actuation systems. A first fractional actuator can be combined with at least one other fractional actuator so that the set of fractional actuators, operating together, meets the maximum torque requirement of the mechanical joint.

Single, 100% actuator systems can have a disadvantage in that all of the actuator must be activated all of the time. Unless the actuator is operating at its optimum design point, it is wasting energy. In a hydraulic system using a hydraulic cylinder sized to the maximum torque requirement, for example, the wasted energy can be embodied in the excess high-pressure hydraulic fluid that is used to move the hydraulic piston under little or no load. Moreover, as the motion of the actuator may be excessively fast even when there is a load to press against, the high-pressure fluid is often throttled by a pressure control or servo valve so that the support member moves at a slower, more desirable pace. Both the use of excess fluid and throttling are examples of wasting the potential energy contained in the pressurized hydraulic fluid.

A mechanical joint can overcome the inherent disadvantages of the prior art by splitting the single actuator per DOF into two or more fractional actuators per DOF. In essence, using a plurality of fractional actuators creates a gear shifting scenario in which the one or more actuators can be selectively recruited to efficiently meet all the operating scenarios that may be required of the joint. Thus, at any particular operating condition which is less than the maximum design torque condition for the joint, one or the other or both of the fractional actuators can be operating near its optimum and most efficient design point.

The fractional split between a two fractional antagonistic actuator system can range anywhere from 95/5 to 50/50, and can further vary among the locations of the biomimetic mechanical joints throughout the humanoid robotic body. The optimum ratio will depend upon the performance boundary conditions of the mechanical joint, and will vary considerably upon the designated purpose of the robotic body (e.g. general purpose, heavy lifting, running, climbing assist, etc.) and the type and configuration of the actuators in the actuator system. However, a biomimetic mechanical joint with two fractional antagonistic actuators configured for optimal efficiency can have a fractional split generally ranging between 80/20 and 60/40.

One reason for the improved efficiency is that fractional antagonistic actuators creating motion about each DOF axis can better emulate the structure of the human body, which naturally uses only just enough muscle to meet the performance required of the joint or limb at any particular time. In other words, energy is conserved in a human joint by selectively recruiting, or activating, only the muscles or muscle groups needed to move the attached support member in the desired manner. When combined with a VR pulley, furthermore, the resulting present invention mechanical joint employing both selectively recruitable fractional actuators in combination with a VR pulley can more closely emulate both the performance and efficiency of a natural joint.

Each of the above-recited advantages will be apparent in light of the detailed description set forth below and best understood with reference to the accompanying drawings, wherein the elements and features of the invention are designated by numerals throughout. These advantages are not meant to be limiting in any way. Indeed, one skilled in the art will appreciate that other advantages may be realized, other than those specifically recited herein, upon practicing the present invention.

Figure 1:
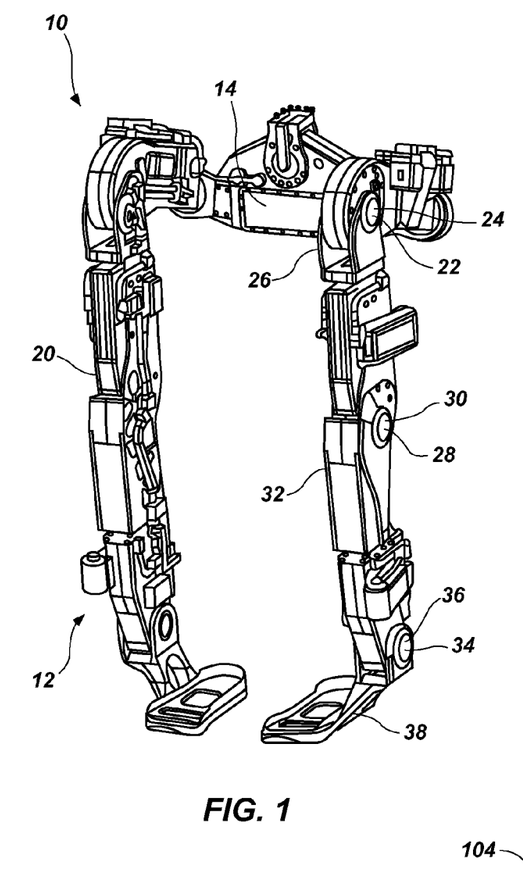
FIG. 1 illustrates a perspective view of an exemplary exoskeleton which can provide a platform for the biomimetic mechanical joint of the present invention.

Illustrated in FIG. 1 is an exemplary embodiment of an exoskeleton 10, which can provide a platform for the various embodiments of the biomimetic mechanical joints of the present invention. The exoskeleton has the potential to provide mechanical assistance to humans in variety of situations, including increased mobility for the handicapped, augmented physical labor, and enhanced soldiering activities. As shown, the exoskeleton can include a whole-body support frame. In another embodiment it can also include a partial body frame, such as the lower body walking portion, or can even be embodied in individual limbs. The biomimetic mechanical joint can be applied to any load-carrying support member on the exoskeleton, and is especially suitable for one or more joints in the legs or lower half of the body.

As shown in FIG. 1, the exoskeleton 10 can include a lower body portion 12. The lower body portion can include a pelvic region 14 to which are attached the two legs 20, each of which can be further comprised of a hip joint 22, a knee joint 28 and an ankle joint 34. For the purposes of this application, the biomimetic mechanical joint can be defined as the assembly which includes the pivot device, the attached rotary support member and the actuator sub-assembly. The actuator sub-assembly can often be mounted inside the rotary support member. The biomimetic mechanical hip joint 22 can therefore comprise the hip pivot device 24 and the upper leg or thigh support member 26, the knee joint 28 can comprise the knee pivot device 30 and the lower leg or calf support member 32, and the ankle joint 34 can comprise the ankle pivot device 36 and the foot support member 38.

Figure 2:
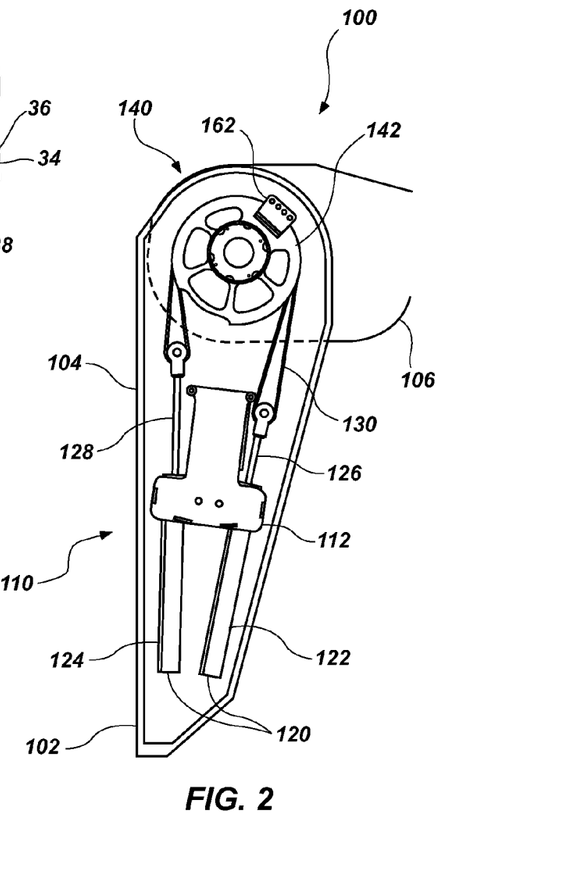
FIG. 2 illustrates a side view of a biomimetic mechanical joint, according to an exemplary embodiment of the present invention.

Illustrated in FIG. 2 is a side view of one exemplary embodiment 100 of a biomimetic mechanical joint that could be applied to any of the load bearing joints of the exoskeleton or biomimetic robotic device. The biomimetic mechanical joint 100 can have a rigid outer shell 104 surrounding the pivot device 140, or variable-radius ("VR") pulley 142, and forming the rotary support member 102 of the mechanical joint.

Antagonistic actuators, in this case a single antagonistic actuator pair 120 utilizing two single-acting hydraulic actuators 122, 124 can be included in an actuator sub-assembly 110 that is driven by a hydraulic control system mounted within a control module 112 located between the antagonistic actuators. A flexible tendon 130 can be coupled at both ends to hydraulic actuator pistons 126, 128 extending from the antagonistic actuator pair 120, and at a midsection to a tendon attachment block 162 mounted to the VR pulley. In another aspect of the invention the tendon 130 can be separated into two shorter tendons, with one end of each shorter tendon coupled to a tendon attachment point on the VR pulley and the other end to one of the actuators in the antagonistic actuator pair.

While the antagonistic actuator 120 illustrated in FIG. 2 can comprises two single-acting linear hydraulic actuators 122, 124 coupled together around the VR pulley 142 with a flexible tendon 130, the antagonistic actuator driving the biomimetic mechanical joint of the present invention can further comprise single-acting pneumatic actuators, linear electric motors, rotary electric motors, or any other pair of uni-directional actuators (e.g. able to generate a force in only one direction) that are capable of being coupled about the VR pulley via a flexible tendon.

In the exemplary embodiment 100 of the biomimetic mechanical joint shown in FIG. 2, actuator sub-assembly 110 can be mounted to the inside of the rigid shell 104 of the rotary support member 102, while the VR pulley can be fixed relative to a base support member 106. By way of an illustrative example, if the biomimetic mechanical joint were integrated into the hip joint of the exoskeleton of FIG. 1, the joint's actuator sub-assembly could be mounted to the inside of the upper leg or thigh support member while the hip VR pulley was fixed relative to the pelvic region. In an alternative aspect of the biomimetic mechanical joint, however, the actuator sub-assembly can be mounted to the base support member 106 (in this case the pelvic region) and the VR pulley 142 can be fixed relative to the rotary support member 102 (or the upper leg support member).

Although many of the embodiments described herein locate the actuator sub-assembly 110 inside the rotary support member 102, either configuration can allow for powered rotation of the rotary support member 102 relative to the base support member 106 by the biomimetic mechanical joint 100. Furthermore, the base support 106 member can comprise a rigid body section of the biomimetic robotic device, such as the torso, as well as the rotary support member of an adjacent mechanical joint.

Figures 3, 4, 5:
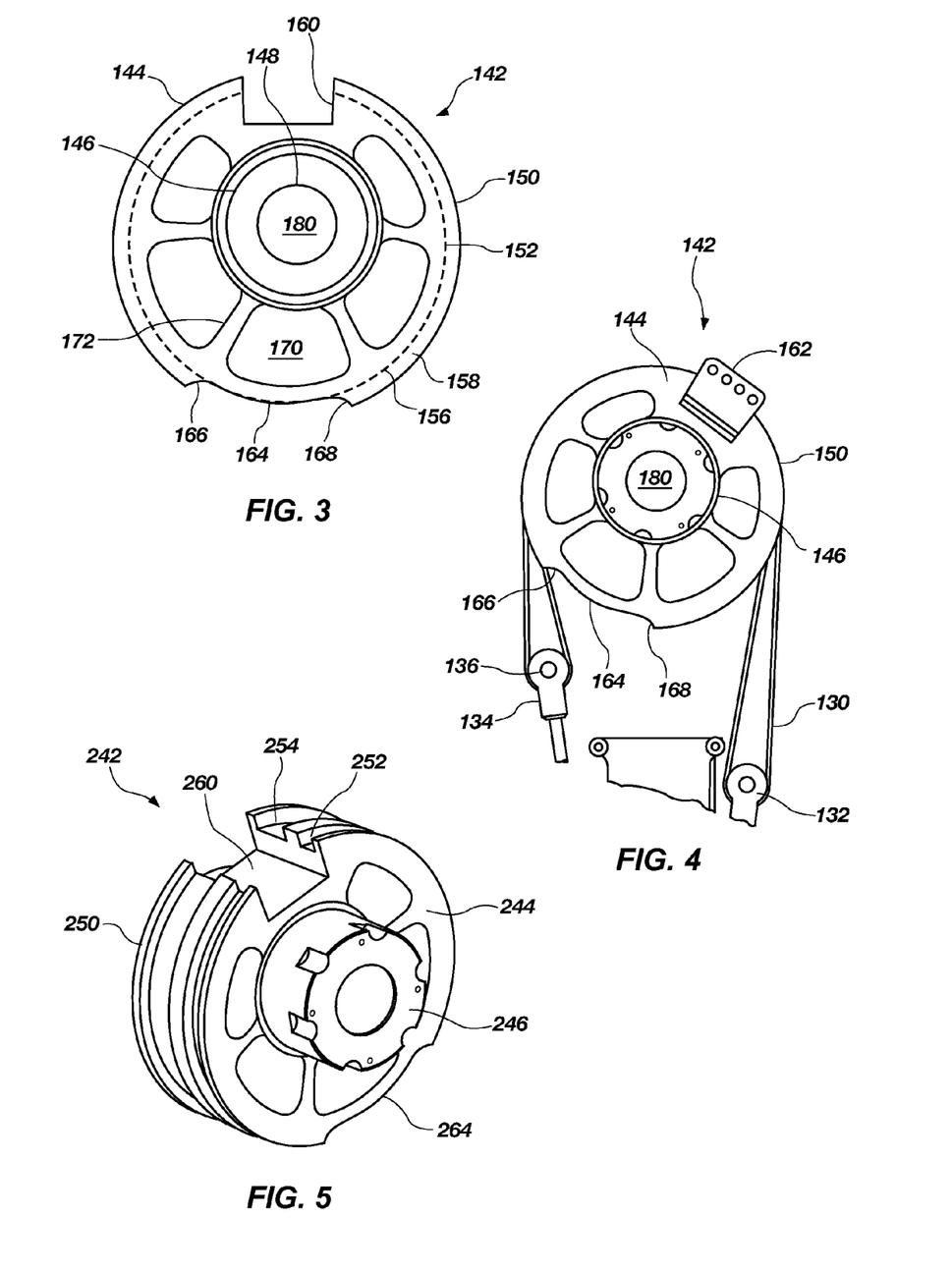
FIG. 3 illustrates a close-up side view of a variable radius pulley, according to the embodiment of FIG. 2.
FIG. 4 illustrates a close-up side view of a variable-radius pulley and tendon system, according to the embodiment of FIG. 2.
FIG. 5 illustrates a perspective side view of a variable radius pulley having two tendon grooves.

A close-up side view of the VR pulley 142 is shown in FIGS. 3 and 4. The VR pulley can comprise a disc portion 144 and an axle portion 146, and can rotate about a pivot post 180 which fits inside a center hole 148 in the axle portion of the VR pulley. Situated within either or both the pivot post 180 or the center hole 148 can be a rotating interface such as a bearing or a bushing (not shown), which allows the VR pulley and the pivot post to rotate relative to each other.

The disc portion 144 can have an circumferential outer surface 150 into which a tendon groove 152 can be formed. The tendon groove can have a landing surface 156 for contacting the tendon, and sidewalls 158 for preventing the tendon from sliding off the VR pulley. An attachment slot 160 can be formed in the disc portion 144 which axially bisects the tendon groove 152 and provides a location for a tendon attachment block 162 to be mounted to the pulley. Hollow pockets or voids 170 can also be formed in the disc portion to reduce the weight of the VR pulley, and can have structural ribs 172 of different lengths providing support for the outer landing surface.

The circumferential outer surface 150 of the VR pulley 142 can be round, with the center hole 148 formed in a location that is off-set or eccentric from the geometric center of the round outer surface or disc body 144. The center hole 148 can further define the pivot point about which the VR pulley 142 rotates, so that the radial distance between the outer surface and the pivot point is variable along the length of the outer surface 150. Thus, a round pulley with an eccentric center hole 148 and axle portion 146 can form a VR pulley, as shown. In another aspect of the present invention, the VR pulley's disc body and outer surface may not be round, but instead can be an oblong, elliptical or some other non-round body or shape that provides the VR pulley with a continuously variable radius having more or less eccentricity than the round embodiment 142 with an eccentric pivot point illustrated in FIGS. 3-4.

The VR pulley 142 can include a cut-out notch 164 in the disc portion 144 that is diametrically opposite the attachment slot 160 and attachment block 162. Within the cut-out the sidewalls 158 of the tendon groove 152 can be removed down to the level of the landing surface 156, resulting in a notch that is substantially flush with the landing surface of the tendon groove. Either end of the cut-out can have a corner radius 166, 168 that can match the round profiles of end connectors 132, 124 mounted to the ends of the actuator pistons. (see FIG. 4). Thus, the corner radius of the cut-out can be configured to partially receive the end connectors when the VR pulley has been rotated to either furthest rotational position. Referring to FIG. 4, the corner radius 168 of the cut-out notch can receive the rounded end-connector 134 when the VR pulley is rotated to its furthest clock-wise position. Likewise, the corner radius 166 of the cut-out can receive the rounded end-connector 132 when the VR pulley is rotated to its furthest counter clockwise position.

Providing the VR pulley with a cut-out having corner radii can advantageously extend the range of rotation of the biomimetic mechanical joint by a few degrees in either direction, as well as avoid jerking the tendon and the actuator sub-assembly if the actuator piston reaches its furthest limits and abuts the VR pulley.

The first and second end portions of the tendon 130 can be attached to the tips of the actuator pistons by any means available in the art. In the embodiment shown, for example, the tendon can be made sufficiently long so that the ends can be looped around or through the end connectors 132, 134 and connected back to the attachment block 162. Moreover, the end connectors can be configured with connector rods 136 that fit within the tendon loops and secure the tendon to the end connectors. The looped configuration can be advantageous by allowing for small movements of the tendon relative to the actuator pistons during operation, as the tendon is alternately wrapped and unwrapped around the VR pulley. These movements can relieve stress and reduce wear, and further ensure that the load acting on the antagonistic actuators is in pure tension.

Illustrated in FIG. 5 is a perspective side view of a VR pulley 242 having two tendon grooves 252, 254 formed in the circumferential outer surface 250, for application with exemplary embodiments of the biomimetic mechanical joint utilizing actuation systems with two tendons. As can be seen, the tendon grooves can be formed to hold tendons of varying size, and where the large groove 254 can be configured to hold a tendon that is significantly wider than the small groove 252. Both the attachment slot 260 and the diametrically opposed cut-out notch 264 can transversely bisect both tendon grooves. The tendon grooves 252, 254 can have diameters D1 and D2, respectively, which can be substantially equal in diameter.

In another aspect of the present invention, the large tendon groove 254 can have a diameter which is smaller than the diameter of the small tendon groove 252, so as to provide a different mechanical advantage for each tendon and antagonistic actuator pair. In yet another aspect, the VR pulley can be formed with a small tendon groove 252 and large tendon groove 254 having non-circular or elliptical shapes that are not aligned with each other and may or may not having differing diameters, respectively. The differences in the sizes and/or shapes and/or orientations between the two tendon grooves can be used in combination with differences in the sizing of the antagonistic actuators or antagonistic actuator pairs, as described in more detail below, to provide additional flexibility in modifying and extending the performance characteristics of the mechanical joint. Consequently, the variable torque characteristics of the biomimetic mechanical joint can become dependent upon the direction of rotation, leading to a mechanical joint that better emulates performance and efficiency of a natural joint.

Figures 6, 7:
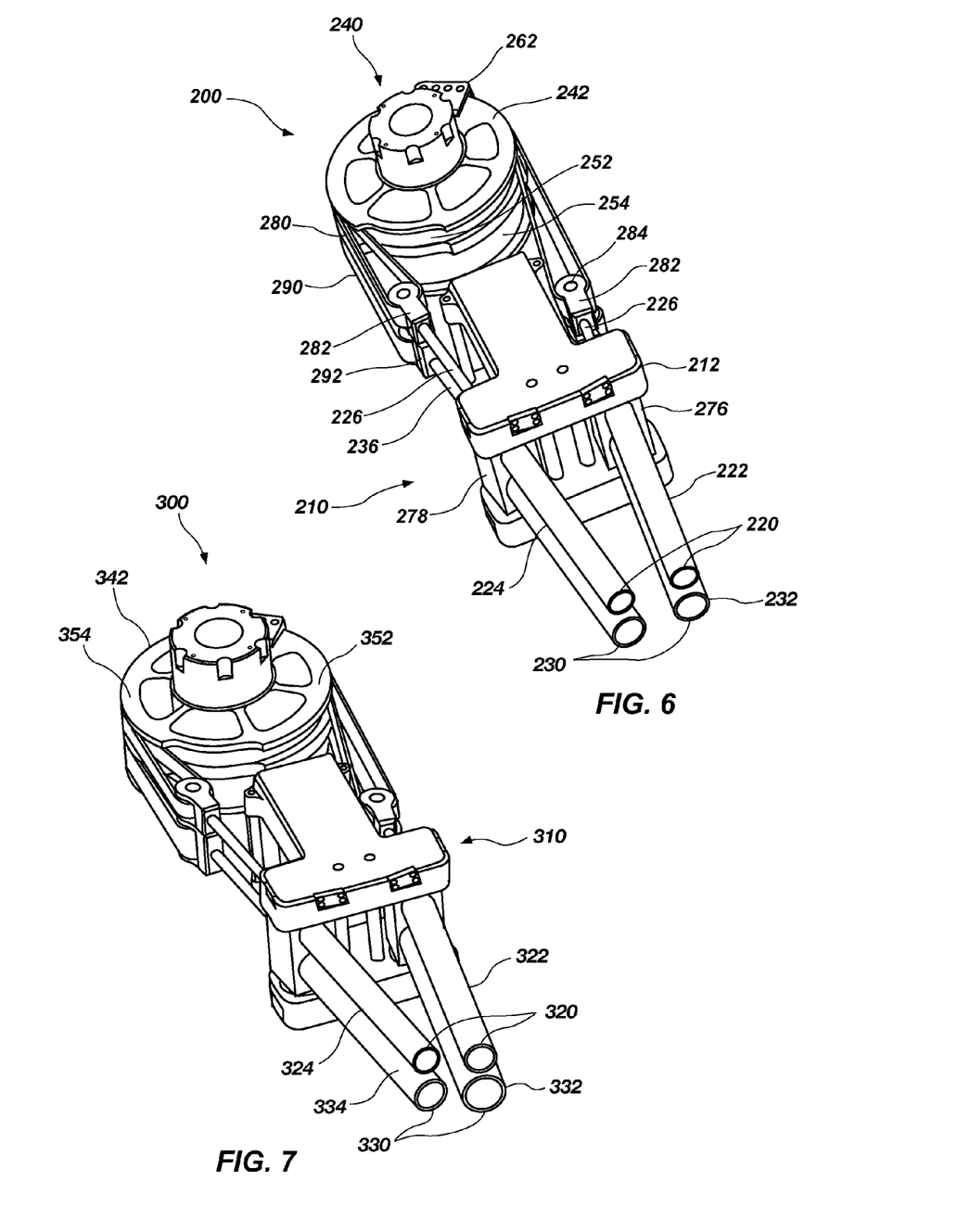
FIG. 6 illustrates a perspective view of a biomimetic mechanical joint, according to another exemplary embodiment of the present invention.
FIG. 7 illustrates a perspective view of a biomimetic mechanical joint, according to yet another exemplary embodiment of the present invention.

One exemplary embodiment 200 of the biomimetic mechanical joint which utilizes two tendons and the dual-grooved VR pulley is illustrated in FIG. 6, without the rigid outer shells of the rotary or base support members. The biomimetic mechanical joint can include two antagonistic actuator pairs 220, 230. The two actuators and the tendon comprising either antagonistic actuator can be considered a single antagonistic actuator pair, since each individual actuator is a linear, single-acting device that can only rotate the VR pulley 242 in one direction. Furthermore, each antagonistic actuator pair in the exemplary biomimetic mechanical joint 200 can have symmetric actuators, meaning that both single-acting actuators in the same pair are of similar size and configuration, allowing the actuator pair to provide symmetric movement in both directions.

In another exemplary embodiment, the antagonistic actuator pairs can comprise fractional actuators of different sizes such as a large actuator pair 230 and a small actuator pair 220, which as described above, can be operated together to meet the maximum torque requirement of the mechanical joint. If the fractional actuators are hydraulic cylinders, the small actuator pair 220 can be provided with small diameter hydraulic cylinders 222, 224 that are sized for a different operating state than the actuators 232, 234 of the large actuator pair. It can be appreciated that, for a given flowrate of hydraulic fluid from a control body 212, a smaller hydraulic piston area will rotate the VR pulley faster than a larger hydraulic piston area, but with reduced force. Thus, the larger diameter actuator pair will rotate the VR pulley at a slower rate with the same flowrate of hydraulic fluid, but can provide more pulling force on the tendon since the force imparted by the actuator is directly proportional to the area of the hydraulic piston.

The two symmetrically-sized actuators of each fractional antagonistic actuator pair 220, 230 can be linked together over the VR pulley 242 with tendons 280, 290. Although the tendons may be provided in a variety of shapes sizes, the tendons shown in the embodiment 200 can have a belt-shaped profile of defined width and thickness, and can further be configured with dimensions that match with the width and thickness of the corresponding tendon grooves 252, 254. Each tendon can be coupled at its midsection to the attachment block 262 connected to the VR pulley, which device can fix the tendons to the VR pulley and prevent slippage of the tendons within the grooves.

In the embodiment 200 shown, the tendons 280, 290 can be attached to the ends of the actuator pistons 226, 236 by looping the tendons through end connectors 282, 292 and coupling the ends of the tendons back to the coupling block 262. Additionally, each end connector can be configured with a connector rod 284 that fits within the tendon loops and secure the tendons to the end connectors. Other means for coupling the tendons to the fractional antagonistic actuators can be appreciated by one of skill in the art, and are considered to fall within the scope of the present invention.

To allow for more efficient operation, the fractional actuators can be selectively recruited and disengaged from powering the biomimetic mechanical joint. Consequently, the two tendons 280, 290 can be separately attached to their respective antagonistic actuator pair 220, 230 with the end connectors 282, 292 to allow relative movement between the two tendons in response to varying load conditions, e.g. a loaded tendon can stretch more than an unloaded tendon.

For instance, if the large actuator pair 230 is active and the small actuator pair 220 is inactive or disengaged, the segment of the larger tendon 290 attached to the working large actuator 232 can stretch slightly under load, while the segment of the smaller tendon 280 for the adjacent small actuator 222 can remain slack. Even though both tendons can be fixed to the VR pulley 242 with the attachment block 262, only the segment of the tendon 290 connected to the working, large actuator 232 may pull on and rotate the VR pulley. On the opposite side of the actuator sub-assembly 210, however, actuator pistons 226, 236 of both the small 224 and large inactive 234 actuators can follow the movement of their respective tendons 280, 290 as they roll up onto the VR pulley rotating under the influence of the active working actuator 232.

In an alternative embodiment, the tendons 280, 290 can be linked together at the end connectors 282, 292 such as with an extra-long, common connector rod 284. And in another alternative embodiment (not shown), the two antagonistic actuator pairs can share a common end connector coupled to a single, double-wide tendon-belt. Linking the end connectors or using a double-wide tendon belt can ensure that the inactive actuator follows the active actuator during rotation of the mechanical joint, and can be maintained in a position for ready activation at any moment in time.

Combining the VR pulley 242 with selectively recruitable fractional actuators 220, 230 can result in a biomimetic mechanical joint 200 that closely emulates both the performance and efficiency of a natural joint. For instance, a VR pulley 242 can facilitate the rotation of the rotary support member about the base support member by creating a mechanical advantage between the pivot device 240 and the actuation sub-assembly 210 during the high-torque operating conditions. This can effectively reduce and smooth out the power requirements for driving the mechanical joint 200 across its entire range of motion and under a variety of load conditions, and allow for the selection of a smaller and less-powerful (e.g. less-demanding and energy-consuming) antagonistic actuator to drive the mechanical joint and still meet required performance criteria.

Breaking up the single antagonistic actuator into two or more fractional antagonistic actuator pairs 220, 230, furthermore, allows the actuator sub-assembly 210 to meet the reduced power requirements provided by the VR pulley in a more efficient manner. The fractional actuators can be selectively recruited or disengaged according to the instantaneous speed and torque requirements on the mechanical joint 200, so that either the small antagonistic actuator pair 220 or the large antagonistic actuator pair 230 or both are utilized to meet the desired performance.

A method for sizing the fractional actuators to meet the projected speed and torque requirements of the biomimetic mechanical joint is described in commonly-owned and co-pending patent application Ser. No. PCT/US09/55440, filed Aug. 28, 2009, and entitled "Method Of Sizing Actuators For A Biomimetic Mechanical Joint", which application is incorporated by reference in its entirety herein.

It can be appreciated that as the VR pulley 142 is rotated by the actuation sub-assembly 210 that the alignment of the point of contact between the tendons 280, 290 and the VR pulley, the end connectors 282, 292 and the long axis of the antagonistic actuators 220, 230 can change, due to the variation in the radius of the VR pulley. Moreover, the shift in alignment can be different for each side of the actuator sub-assembly. To ensure that no harmful twisting moments or lateral forces are impressed on the actuator pistons 226, 236 in consequence to the shifting alignment, the piston ends (or other portion (e.g., midsection)) of the actuators on either side of the control body 212 can be mounted into swivel blocks 276, 278 that can rotate relative to the control module. The swivel blocks can provide the actuators with the freedom to pivot around their piston ends (or e.g., midsection, upper end, etc.) to maintain correct alignment between the long axis of the actuators, the end connectors, and the tangential contact point between the tendons and the VR pulley. In another aspect of the present invention, the control module can be lengthened so that the solid ends (e.g. opposite side from the actuator piston) of the actuators can be mounted into swivel blocks, allowing the pivoting to take place at the base of the actuator sub-assembly rather than at the mid-span.

If either the fractional actuators, or antagonistic actuator pairs 220, 230, is selectively recruited at any particular moment in time to power the biomimetic mechanical joint 200, the actuator not recruited at that instant can be selectively disengaged from the mechanical joint to prevent unnecessary drag on the active portion of the actuator system. This selective disengagement can include a fluidic (e.g. hydraulic or pneumatic) disengagement between the actuators and a fluid supply, an electrical disconnection between a linear or rotary motor and a power supply, or a physical disconnection between the antagonistic actuators and the VR pulley, etc.

As described above, in one aspect of the embodiment 200 of the present invention illustrated in FIG. 6, each individual actuator in each antagonistic actuator pair 220, 230 can be a single-acting, linear hydraulic actuator. Each actuator, furthermore, can be fluidicly connected to a pressure control valve (PCV) operable with a pilot valve located inside the control body 212. The PCVs and pilot valves can be configured so that the inactive antagonistic actuator pair operates in accordance with a "slosh" mode, which allows the hydraulic fluid contained in the inactive antagonistic actuator pair to shunt back and forth between the two single-acting hydraulic cylinders without consuming or performing work. In other words, the inactive fractional actuator can be configured for idle operation by selecting the PCVs and pilot valves for slosh mode, which can disengage the fractional actuator from the system so that it does not contribute as a drag or brake on the biomimetic mechanical joint.

The hydraulic system which can utilize two antagonistic actuator pairs, in conjunction with corresponding PCVs and pilot valves, to allow for active operation of one actuator pair and slosh mode operation of the other, is described in more detail in commonly-owned and co-pending U.S. patent application Ser. Nos. 12/074,261, filed Feb. 28, 2008, entitled "Fluid Control System Having Selective Recruitable Actuators;" and 12/074,260, filed Feb. 28, 2008, entitled, "Antagonistic Fluid Control System for Active and Passive Actuator Operation," which applications are incorporated by reference in their entirety herein.

In another aspect of the present invention, it may also be possible for both fractional actuators 220, 230 to be continuously throttled, such as with a valve module (not shown), when driving the mechanical joint 200. Consequently, it is to be appreciated that a biomimetic mechanical joint having the capability for the continuous throttling and the selective recruitment and/or disengagement of a plurality of fractional actuators results in an actuation or drive system with two control degrees-of-freedom. This flexibility in operating the actuator system can be advantageous over the prior art by allowing the mechanical joint to reach various operating points with one or more actuator recruitment configurations and throttle settings, from which the most efficient can be selected.

A method of operating a plurality of fractional actuators having the capability for both selective recruitment/disengagement and continuous throttling, to meet the instantaneous speed and torque operating requirements of a biomimetic mechanical joint, is described in commonly-owned and co-pending patent application Ser. No. PCT/US09/55423, filed Aug. 28, 2009, and entitled "Control Logic for Biomimetic Joint Actuators", which application is incorporated by reference in its entirety herein.

In yet another aspect of the present invention (not shown), the biomimetic mechanical joint can be configured with a single uni-directional actuator coupled to a single flexible tendon that is connected to a tendon attachment point on the VR pulley, and which can operate to actively actuate or rotate the joint in one direction while allowing an applied load (e.g. a weight under the influence of gravity, etc.) to operate the joint in the opposite direction. The uni-directional embodiment of the biomimetic mechanical joint can be useful in a variety of applications, including human-like or natural prosthetic devices that are tailored to a specific task or function. Additionally, in yet another embodiment the uni-directional biomimetic mechanical joint can be provided with two or more tendon/actuator pairs that are connected to the same side of the VR pulley, to allow for the same variable load and speed capabilities described in the antagonistic actuator configuration above. Other variations of the uni-directional biomimetic joint which can appreciated by one of skill in the art are considered to fall within the scope of the present invention.

Illustrated in FIG. 7 is another exemplary embodiment of a biomimetic mechanical joint 300 that can be similar to previous embodiments having a VR pulley 342 powered by two fractional antagonistic actuator pairs. However, the mechanical joint 300 is distinguishable from earlier embodiments in that each individual actuator in both fractional actuators 320, 330 can be sized different from each of the other actuators in the actuator sub-assembly 310, in order to take further advantage of the leveraging aspects of the VR pulley and better emulate the performance of the natural joint. This enhanced variability and flexibility in design can become even more apparent when combined with a VR pulley having tendon grooves of differing sizes and/or shapes/configurations, as described above.

By way of example, the small fractional antagonistic actuator pair 320 can have a large-radius actuator 322 which, when recruited, rotates the VR pulley 342 using a large-radius portion of the 352 of the VR pulley, and a small-radius actuator 324 which, when recruited, rotates the pivot device using the small-radius portion of the 354 of the VR pulley. In a similar fashion, the large, fractional antagonistic actuator pair 330 can have a large-radius actuator 332 and small-radius actuator 334 operating about the large-radius portion 352 and small-radius portion 354 of the variable-radius pulley, respectively.

The large-radius actuators 322, 332 can be differentially sized from their related small-radius actuators 324, 334 to take advantage of the mechanical advantage provided by the VR pulley and better emulate the performance of the natural joint. For instance, a natural joint may be capable of providing greater torque when moved in one direction verses the other (for instance, the quadriceps muscles can be significantly stronger than the hamstring muscles when rotating an upper leg member about the hip joint). When the VR pulley 342 is assembled with an actuator sub-assembly 310 having differentially sized actuator pairs 322, 324 and 332, 334, the performance characteristics of the mechanical joint can be modified and extended, and may become dependent upon the direction of rotation of the mechanical joint. Consequently, the resulting biomimetic mechanical joint can better emulate the performance and efficiency of the natural joint.

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

More specifically, while illustrative exemplary embodiments of the invention have been described herein, the present invention is not limited to these embodiments, but includes any and all embodiments having modifications, omissions, combinations (e.g., of aspects across various embodiments), adaptations and/or alterations as would be appreciated by those in the art based on the foregoing detailed description. The limitations in the claims are to be interpreted broadly based on the language employed in the claims and not limited to examples described in the foregoing detailed description or during the prosecution of the application, which examples are to be construed as non-exclusive. For example, in the present disclosure, the term "preferably" is non-exclusive where it is intended to mean "preferably, but not limited to." Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given above.

What is claimed and desired to be secured by Letters Patent is:

1. A biomimetic mechanical joint for generating a variable torque between support members of a biomimetic robotic device, the mechanical joint comprising:
    a base support member;
    a rotary support member rotably coupled to the base support member;
    a variable-radius pulley operably coupled between the base support member and the rotary support member for facilitating rotation of the rotary support member about the base support member, the pulley comprising:
    a sheave body having a circumferential outer surface and a pivot point, the radial distance between the outer surface and the pivot point being variable along a length of the outer surface;
    at least one tendon groove formed in the outer surface, the tendon groove having a tendon landing surface and sidewalls; and
    a tendon attachment point within the at least one tendon groove;
    at least one flexible tendon coupled to the tendon attachment point and having first and second free end portions wrapping around the pulley in opposite directions within the tendon groove; and
    at least one antagonistic actuator pair coupled to the first and second free end portions with a pair of end connectors, the actuator pair being configured to selectively operate the tendon around the pulley in either direction and create a variable torque between the base and rotary support members.

2. The mechanical joint of claim 1, further comprising a cut-out in the sidewalls of the sheave body substantially opposite the tendon attachment point, the cut-out being configured to receive an end connector when the pulley is rotated to either furthest rotational position.

3. The mechanical joint of claim 1, wherein each actuator of the antagonistic actuator pair is pivotally supported to undergo pivotal motion and maintain alignment between a long axis of the actuator and a tangential contact point between the tendon and the pulley.

4. The mechanical joint of claim 1, wherein the sheave body of the pulley is circular and the pivot point is eccentric from the center of the circle.

5. The mechanical joint of claim 1, wherein the tendon attachment point further comprises a tendon attachment block inserted into a transverse slot formed in the circumferential outer surface of the sheave body.

6. The mechanical joint of claim 1, wherein each of the first and second free end portions is looped around an end connector and a tip of the free end portion is coupled to the tendon attachment point.

7. The mechanical joint of claim 1, wherein the sheave body is fixed relative to the base support member and the actuator pair is coupled to the rotary support member.

8. The mechanical joint of claim 1, wherein the antagonistic actuator pair is coupled to the base support member and the sheave body is fixed relative to the rotary support member.

9. The mechanical joint of claim 1, wherein the base support member comprises one of a torso of the biomimetic robotic device, and a rotary support member of an adjacent biomimetic mechanical joint.

10. A biomimetic mechanical joint for generating a variable torque between support members of a biomimetic robotic device, the mechanical joint comprising:
    a base support member;
    a rotary support member rotatably coupled to the base support member;
    a variable-radius pulley operably coupled between the base support member and the rotary support member for facilitating rotation of the rotary support member about the base support member, the variable-radius pulley comprising:
    a sheave body having a circumferential outer surface and a pivot point and a radial distance between the outer surface and the pivot point being variable along a length of the outer surface;
    a tendon groove formed in the outer surface; and
    at least one tendon attachment point within the tendon groove;
    at least one flexible tendon coupled to the tendon attachment point and having a free end portion wrapping around the pulley within the tendon groove; and
    at least one actuator coupled to the free end portion and configured to pull the tendon around the variable-radius pulley to create a variable torque between the base and rotary support members.

11. The mechanical joint of claim 10, wherein the at least one flexible tendon comprises first and second flexible tendons, each tendon coupled to a tendon attachment point and having a free end portion wrapping around the pulley in an opposite direction from the other and coupling to an actuator of an antagonistic actuator pair, the actuator pair being configured to selectively pull the tendons around the variable-radius pulley in either direction.

12. The mechanical joint of claim 10, wherein the flexible tendon further comprises an intermediate portion coupled to the tendon attachment point, and first and second free end portions wrapping around the pulley in opposite directions and coupling to an actuator of an antagonistic actuator pair, the actuator pair being configured to selectively pull the tendon around the variable-radius pulley in either direction.

13. A method of making a biomimetic mechanical joint for generating a variable torque between support members of a biomimetic robotic device, the method comprising:
- obtaining a base support member and a rotary support member;
- coupling a variable-radius pulley having a pivot means between the base support member and the rotary support member to facilitate rotation of the rotary support member about the base support member;
- mounting at least one antagonistic actuator pair to the rotary support member; and
- installing at least one flexible tendon between the variable-radius pulley and the antagonistic actuator pair, wherein the actuator pair activates to pull the tendon around the variable-radius pulley in either direction to create a variable torque between the base and rotary support members.

14. A biomimetic mechanical joint for generating a variable torque between support members of a biomimetic robotic device, the mechanical joint comprising:
- a base support member;
- a rotary support member rotably coupled to the base support member;
- a variable-radius pulley operably coupled between the base support member and the rotary support member for facilitating rotation of the rotary support member about the base support member, the pulley comprising:
- a sheave body having a circumferential outer surface and a pivot point, the radial distance between the outer surface and the pivot point being variable along a length of the outer surface;
- at least two tendon grooves formed in the outer surface, each tendon groove having a tendon landing and sidewalls; and
- a tendon attachment point within each of the tendon grooves;
- at least two flexible tendons, each tendon being coupled to one of the tendon attachment points and having first and second free end portions wrapping around the pulley in opposite directions within the tendon groove; and
- at least two antagonistic actuator pairs, each actuator pair being coupled to the first and second end portions of one of the at least two tendons with a pair of end connectors, and being configured to selectively operate the tendon around the pulley in either direction to create a variable torque between the base and rotary support members.

15. The mechanical joint of claim 14, further comprising a cut-out in the sidewalls of the sheave body opposite the tendon attachment point, the cut-out being configured to receive an end connector when the pulley is rotated to either furthest rotational position.

16. The mechanical joint of claim 14, wherein one of the antagonistic actuator pairs is larger than the other.

17. The mechanical joint of claim 16, wherein the flexible tendons further comprise tendon belts having a rectangular cross-section, and wherein one of the flexible tendons and corresponding tendon grooves is wider than the other.

18. The mechanical joint of claim 17, wherein each actuator of the at least two antagonistic actuator pairs is individually sized different from any of the other actuators.

19. The mechanical joint of claim 14, wherein the variable radius pulley further comprises a large tendon groove having a different diameter than a small tendon groove to provide a different mechanical advantage to a tendon and actuator pair operable therewith.

20. The mechanical joint of claim 14, wherein the variable radius pulley further comprises a large tendon groove and a small tendon groove, each having a non-circular shape, and each being offset relative to the other, and not aligned.

* * * * *